United States Patent [19]
Sakito et al.

[11] Patent Number: 5,616,769
[45] Date of Patent: Apr. 1, 1997

[54] METHOD FOR PURIFYING O,S-DIMETHYL N-ACETYLPHOSPHORAMIDOTHIOATE

[75] Inventors: Yoji Sakito; Mamoru Shirahata; Yujiro Kiyoshima; Kazuya Minamisaka, all of Oita; Atukazu Iwata, Takatuki, all of Japan

[73] Assignee: Sumitomo Chemical Company, Limited, Osaka, Japan

[21] Appl. No.: 531,751

[22] Filed: Sep. 21, 1995

[30] Foreign Application Priority Data

Sep. 22, 1994 [JP] Japan .................................. 6-227885

[51] Int. Cl.$^6$ ...................................... C07F 9/02
[52] U.S. Cl. ...................... 558/146; 558/178; 558/199
[58] Field of Search ...................... 558/146, 178

[56] References Cited

U.S. PATENT DOCUMENTS

| | | | |
|---|---|---|---|
| 3,896,193 | 7/1975 | Franke | 260/987 |
| 3,917,755 | 11/1975 | Franke | 260/987 |

FOREIGN PATENT DOCUMENTS

| | | |
|---|---|---|
| 516212 | 12/1992 | European Pat. Off. . |
| 48-034583 | 10/1973 | Japan . |
| 64-075494 | 3/1989 | Japan . |
| 539147 | 11/1985 | Spain . |

OTHER PUBLICATIONS

Solov'ev et al., Phosphorus, Sulfur, Silicon Relat. Elem., 57(1–2), 135–41, 1991.

*Primary Examiner*—Johann Richter
*Assistant Examiner*—Laura R. Cross
*Attorney, Agent, or Firm*—Birch, Stewart, Kolasch & Birch, LLP

[57] ABSTRACT

A method for purifying O,S-dimethyl N-acetyphosphoramidothioate, which is characterized by subjecting a crude crystal of O,S-dimethyl N-acetylphosphoramidothioate to recrystallization by using a two-phase solvent system comprising water and an organic which is an aromatic hydrocarbon, an aliphatic carboxylic acid ester or aliphatic ketone, wherein the amount of water is 0.1 to 2 parts by weight and the amount of the organic solvent is 1 to 20 parts by weight to 1 part by weight of the crude O,S-dimethyl N-acetylphosphoramidothioate. A further method for purifying O,S-dimethyl N-acetylphosphoramidothioate, which is characterized by extracting O,S-dimethyl N-acetylphosphoramidothioate from an aqueous solution of crude O,S-dimethyl N-acetylphosphoramidothioate with an organic solvent which is a carbonate ester, an aliphatic carboxylic acid ester, an aliphatic ketone, an aliphatic alcohol or a mixture of two or more thereof, wherein the solubility of water in the organic solvent is in a range of from 1 to 20% by weight, and crystallizing O,S-dimethyl N-acetylphosphoramidothioate from the resulting organic phase.

8 Claims, No Drawings

METHOD FOR PURIFYING O,S-DIMETHYL N-ACETYLPHOSPHORAMIDOTHIOATE

FIELD OF THE INVENTION

The present invention relates to an improved method for purifying O,S-dimethyl N-acetylphosphoramidothioate.

DESCRIPTION OF THE RELATED ART

O,S-dimethy N-acetylphosphoramidothioate is a well-known insecticide, and the production process comprising reacting O,S-dimethylphosphoramidothioate with acetic anhydride in the presence of an acid catalyst to effect the acetylation has been known. O,S-dimethyl N-acetylphosphoramidothioate thus produced was isolated and purified by such a method comprising the steps of extracting the product with chloroform, washing with an aqueous sodium chloride solution and Concentrating the resultant(JP-B48-34583), or by a method comprising neutralizing the reaction solution with an aqueous alkaline solution, extracting the resultant with a halogenated solvent such as dichloromethane or chloroform, and then concentrating the extract to recrystallize(JP-A64-75494).

However, these methods in which halogenated solvents were used has a problem of low productivity in an industrial scale, because the crystalization yield was not satisfactory or the transport of the crystallization slurry solution in a chemical plant was difficult owing to the high concentration of the slurry and the high specific gravity of the solvents. In addition, halogenated solvents have problems over preservation of the environment or environment for working.

Therefore, an object of the present invention is to provide an efficient purification method that can provide O,S-dimethyl N-acetylphosphoramidothioate as a crystal of high purity in a good crystallization yield and transportable recrystallization slurry while without using halogenated solvents.

SUMMARY OF THE INVENTION

The present invention provides a method for purifying O,S-dimethyl N-acetylphosphoramidothioate, which comprises subjecting a crude crystal of O,S-dimethyl N-acetylphosphoramidothioate to recrystallization by using a two-phase solvent system comprising water and an organic solvent which is an aromatic hydrocarbon, an aliphatic carboxylic acid ester or an aliphatic ketone, wherein the amount of water is 0.1 to 2 parts by weight and the amount of organic solvent is 1 to 20 parts by weight per 1 part by weight of crude O,S-dimethyl N-acetylphosphoramidothioate.

The present invention also provides a method for purifying O,S-dimethyl N-acetylphosphoramidothioate, which comprises extracting O,S-dimethyl N-acetyphosphoramidothioate from an aqueous solution of crude O,S-dimethyl N-acetylphosphoramidothioate with an organic solvent which is a carbonate ester, an aliphatic carboxylic acid ester, an aliphatic ketone aliphatic alcohol or a mixture of two or more thereof, wherein the solubility of water in the organic solvent is in a range of from 1 to 20% by weight, and crystallizing O,S-dimethyl N-acetylphosphoramidothioate from the resulting organic phase.

DESCRIPTION OF THE PREFERRED EMBODIMENT

According to the present invention O,S-dimethyl N-acetylphosphoramidothioate can be obtained as a crystal of high purity in a good crystallization yield or as a transportable recrystallization slurry but without using halogenated solvents that are unfavorable.

Description will be made first of the method for purifying O,S-dimethyl N-acetylphosphoramidothioate, which comprises subjecting a crude crystal of O,S-dimethyl N-acetylphosphoramidothioate to recrystallization by using a two-phase solvent system comprising water and an organic solvent which is an aromatic hydrocarbon, an aliphatic carboxylic acid ester or an aliphatic ketone, wherein the amount of water is 0.1 to 2 parts by weight and the amount of organic solvent is 1 to 20 parts by weight to 1 part by weight of crude O,S-dimethyl N-acetylphosphoramidothioate.

O,S-dimethyl N-acetylphosphoramidotioate is usually obtained by acetylating O,S-dimehylphosphoroamidothioate. The acetylation reaction is usually conducted by reacting O,S-dimethylphosphoramidothioate with acetic anhydride in an organic solvent such as toluene, acetic acid or ether or without using a solvent and further in the presence of an acid catalyst such as a protonic acid (e.g. hydrochloric acid, sulfuric acid) or a Lewis acid (e.g. boron trifluoride, aluminum chloride or zinc chloride).

The crude crystal of O,S-diemthyl-N-acetylphosphoramidothioate to be subjected to purification treatment of the present invention may be a solid crude product obtained by the reaction above which contains impurities. The crude crystal may be a crystallized product obtained by cooling the reaction mixture after acetylation reaction, or a solid residue obtained by concentrating the acetylation reaction mixture. The crude crystal usually contains at most about 90% by weight of O,S-dimethyl N-acetylphosphoramidothioate and usually 10 to 30% by weight of unreacted material, by-products and other impurities.

When the acetylation reaction of O,S-dimethylphosphoramidothioate is conducted in a solvent, there occur problems prior to purification steps. For example, a part of the desired product may remain uncrystallized in the solvent used for the crystallization when the acetylation reaction mixture was cooled to form crude crystal, which resulted in a yield reduction; or the efficiency of the concentration is low, because a large amount of reaction solvent must be removed by distillation to obtain solid residue. Therefore, in view of the total yield from O,S-dimethylphosphoramidothioate and production efficiency, a crude crystal product recovered from the acetylation reaction using no solvent or a little solvent if any, and preferably a crystallized product obtained by cooling the said reaction solution are preferred for the purification method of the present invention.

In the present invention, the crude crystal of O,S-dimethyl N-acetylphosphoramidethioate is first subjected to recrystallization using a two-phase solvent system comprising water and a hardly or slightly water soluble organic solvent selected from the group consisting of aromatic hydrocarbon, aliphatic carboxylic acid ester and aliphatic ketone.

As the above-described organic solvents, a $C_6$–$C_{12}$ benzene type compound having a benzene ring which may be unsubstituted or substituted with one or more $C_1$–$C_4$ alkyl group may be preferably used, e.g. benzene, toluene, xylene, ethylbenzene or cumene may be mentioned.

As the aliphatic carboxylic acid ester, a $C_1$–$C_4$, alkyl ester of a $C_1$–$C_4$ aliphatic carboxylic acid is preferably used, and specific examples are propyl formate, isopropyl formate, methyl acetate, ethyl acetate, n-propyl acetate, isopropyl acetate, butyl acetate, methyl propionate, and ethyl propionate.

As the aliphatic ketone, a $C_4$–$C_8$ aliphatic ketone is preferably used, and specific examples thereof are methyl ethyl ketone, methyl n-propyl ketone, methyl n-butyl ketone, methyl isobutyl ketone, diethyl ketone and the like.

In the purification method of the present invention, the amount of water and the organic solvent to be used is critical. The amount of water to be used is 0.1 to 2 parts by weight, preferably 0.1 to 0.5 part by weight, and the amount of the organic solvent to be used is 1 to 20 parts by weight, preferably 1 to 10 parts by weight per 1 part by weight of the crude crystal for the purpose of realizing a good recrystallization yield, high purity and easy transport of slurry solution. If the amount of water or the organic solvent is not within this range, water-soluble impurities may remain unremoved, which results in poor purification or reduction in recrystallization yield.

In the purification method of the present invention, recrystallization treatment is not specially limited, and the recrystallization is usually conducted by a method of mixing the two-phase solvent system comprising water and the organic solvent with crude O,S-dimethyl N-acetylphosphoramidothioate, heating the mixture until the crude solid goes into the solution and then gradually cooling the resultant solution to crystallize. After recrystallization, the resultant mixture is subjected to separation operation such as filtration and the like and then dried e.g. by a conventional method of drying under reduced pressure to yield the desired O,S-dimethyl N-acetylphosphoramidothioate of high purity in a good crystallization yield.

The heating temperature is preferably 80° C. or lower, since a higher temperature may cause decomposition of the desired O,S-dimethyl N-acetylphosphoramidothioate. To dissolve the solid completelyl at the temperature, the amount of water and the kind and amount of the organic solvent to be used are selected and adjusted within the above-specified range of the present invention.

The cooling temperature is usually 30° C. or lower, preferably 10° C. or lower.

The filtrate obtained after separating the crystallized product according to the above-described method can be repeatedly used by adding a crude crystal of O,S-dimethyl N-acetylphosphoramidothioate thereto and then subjecting the resultant solution to the same recrystallization treatment as above to yield a crystal of O,S-dimethyl N-acetylphosphoramidothioate of high purity while maintaining the purity of the crystallized product, as long as the amount of water and the organic solvent is within the above-described range of the present invention.

Next, description will be made on the method for purifying O,S-dimethyl N-acetylphosphoramidothioate, which comprises extracting an aqueous solution of crude O,S-dimethyl N-acetylphosphoramidothioate with a carbonate ester, aliphatic carboxylic acid ester, aliphatic ketone, aliphatic alcohol or a mixed solvent thereof, wherein the solubility of water to the solvent is in a range of from 1 to 20% by weight, followed by subjecting the resultant solution to crystallization.

The aqueous solution of crude O,S-dimethyl N-acetylphosphoramidothioate to be treated is usually obtained by directly adding water to the reaction mixture resulting from the acetylation reaction of O,S-dimethyl phosphoramidothioate, or preferably a neutralized aqueous solution obtained by adding aqueous alkaline solution to the said reaction mixture to neutralize remaining acid components accompanying the acetylation reaction. As an example of an alkaline solution to be used for the neutralization treatment, aqueous ammonia, aqueous caustic soda, aqueous caustic potash and aqueous sodium carbonate solution can be mentioned. These aqueous alkaline solution which are usually used in an industrial process can be used for the purifying treatment of the present invention without any adverse effect.

The aqueous solution to be treated by the present invention is not limited to those mentioned above, and includes an aqueous solution of crude O,S-dimethyl N-acetylphosphoramidothioate obtained by dissolving crude O,S-dimethyl N-acetylphosphoramidothioate in water or the aqueous alkaline solution as described above.

The extracting solvent to be used may be a carbonate ester, aliphatic carboxylic acid ester, aliphatic ketone, aliphatic alcohol or a mixture of two or more thereof wherein the solubility of water to the solvent is in a range of from 1 to 20% by weight at 20° C.

In the method of the present invention it is critical to use the solvents having the above specified characteristics. This is because hydrocarbon solvents such as benzene, toluene and hexane can not be practically used because of the scarce solubility of O,S-dimethyl N-acetylphosphoramidothioate to those solvents. Although methanol, ethanol or acetone are aliphatic alcohols or aliphatic ketones respectively, they can not be used to extract O,S-dimethyl N-acetylphosphoramidothioate from an aqueous solution of crude O,S-dimethyl N-acetylphosphoramidothioate, because they can well dissolve O,S-dimethyl N-acetylphosphoramidothioate, but they are well misible with water at the same time.

The carbonate ester is preferably a ($C_1$–$C_4$, alkyl) ($C_1$–$C_4$ alkyl) carbonate, e.g. dimethyl carbonate, diethyl carbonate or dipropyl carbonate.

The aliphatic carboxylic acid ester is preferably a $C_1$–$C_4$ alkyl ester of a $C_1$–$C_4$ aliphatic carboxylic acid, e.g. ethyl formate, propyl formate, n-propyl acetate, isopropyl formate, methyl acetate, ethyl acetate, isopropyl acetate, butyl acetate, methyl propionate or ethyl propionate.

The aliphatic ketone is preferably a $C_4$–$C_8$ aliphatic ketone, e.g. methyl ethyl ketone, methyl n-propyl ketone, methyl n-butyl ketone, methyl isobutyl ketone or diethyl ketone.

The aliphatic alcohol is preferably isobutyl alcohol and n-pentyl alcohol.

Especially preferred solvents are ethyl acetate and methyl isobutyl ketone.

The amount of solvent to be used varies according to the kind of the solvent and is usually 0.3 to 10 parts by weight per 1 part by weight of the aqueous solution to be extracted.

The extracting operation is carried out by a usual method, for example, a method of mixing the specified solvent of the present invention and aqueous solution of crude O,S-dimethyl N-acetylphosphoramidothioate and then stirring, or passing the solution and the solvent continuously through extraction column in concurrent or counter-current direction and then separating to obtain an organic phase and a water layer. Any optional method can be taken for the extracting operation.

The temperature of extraction operation varies according to the kind and amount of the solvent and is not specifically limited as long as it is lower than the boiling point of the solvent. The temperature is usually 70° C. or lower, preferably 50° C. or lower because a higher temperature may bring about decomposition of the product.

The extraction operation gives an organic phase containing some water, which may be subsequently cooled to crystallize O,S-dimethyl N-acetylphosphoramidothioate according to the extraction conditions such as the kind and amount of the solvent and extraction temperature, but a usually adopted method comprises concentrating the solution by distillating a part of the solvent to yield a concentrate and then cooling the concentrate to crystallize.

The concentration operation varies depending on the kind of the solvent to be used and is usually conducted so that the concentration of O,S-dimethyl N-acetylphosphoramidothioate is 10 to 50% by weight. The temperature of the concentration is usually 70° C. or lower to avoid the decomposition of the product and under reduced pressure, if necessary.

The cooling is usually conducted by stirring the concentrate, and the temperature is determined depending on the concentration degree. The temperature is usually −10° to +30° C.

The present invention will be further explained in detail by the following examples but are not to be construed as limiting the invention thereto.

PREPARATION EXAMPLE OF CRUDE O,S-DIMETHYL N-ACETYLPHOSPHORAMIDOTHIOATE 95.2 Grams of dimethyl sulfate were gradually added to 1500 g(purity 86.3%) of O,O-dimethylphosphoramidothioate and the resultant was further reacted for 6 hours to effect the isomerization reaction to O,S-dimethylphosphoramidothioate. 41 Grams of 98% conc. sulfuric acid and 1218 g of acetic anhydride were separately but at the same time added to the reaction mixture at 40° C. and further reacted for 2 hours. The obtained reaction solution was cooled to 10° C., and the crystallized product was collected to give 805 g of crude O,S-dimethyl N-acetylphosphoramidothioate. The purity of the product was 86%.

EXAMPLE 1

50 Grams of the crude crystal of O,S-dimethyl N-acetylphosphoramidothioate obtained in the above described reaction were added to a mixed solvent consisting of 10 g of water and 100 g of toluene, and the resultant solution was heated to 40° C. under stirring to dissolve the crystal. Then the solution was cooled gradually to 10° C. to obtain a crystallization slurry. The resultant crystal was filtered at the same temperature. The collected crystal was dried under reduced pressure to yield 26.7 g of O,S-dimethyl N-acetylphosphoramidothioate(purity 98.5%, purification yield 61.5%). The slurry concentration of the crystallized mass was 16.3%, and the transport of the slurry was easy.

EXAMPLE 2

30 Grams of the crude crystal O,S-dimethyl N-acetylphosphoramidothioate obtained in the Preparation Example 1 above were added to the filtrate as it is obtained in the Example 1 and the resultant solution was heated to 40° C. to dissolve the crystal under stirring. Then the solution was cooled gradually to 10° C. to crystallize, the resultant crystal was filtered at the same temperature. The collected crystal was dried under reduced pressure to yield 25.8 g of O,S-dimethyl N-acetylphosphoramidothioate (purity 98.1%, purification yield 98%, Overall purification yield of Examples 1 and 2 was 75%).

EXAMPLE 3 to 5

Except that the mixed solvents described in the Table 1 were used in place of the mixed solvent of Example 1, the recrystallization was conducted in the same manner as in the Example 1. The results are shown in Table 1.

TABLE 1

| Exp. No. | Organic solvent (g) mixed with water (10 g) | Purification Yield (%) | Purity (%) | Slurry concentration (%) |
|---|---|---|---|---|
| 3 | Methyl isobutyl ketone (100 g) | 76.2 | 99.2 | 19.1 |
| 4 | Ethyl acetate (100 g) | 61.9 | 98.4 | 16.7 |
| 5 | Xylene (100 g) | 61.5 | 99.3 | 16.6 |

COMPARATIVE EXAMPLE 1

To 50 g of the crude crystal O,S-dimethyl N-acetylphosphoramidothioate obtained in the above-described preparation was added 15 g of water and the resultant solution was heated to 40° C. to dissolve the crystal under stirring. Then the solution was cooled gradually to 5° C. to crystalize, the resultant crystal was filtered at the same temperature. The collected crystal was dried under reduced pressure to yield 10.8 g of O,S-dimethyl N-acetylphosphoramidothioate (purity 94.5%, purification yield 24%, Slurry concentration of the crystallization mass: 16.7%).

COMPARATIVE EXAMPLE 2

To 50 g of crude crystal O,S-dimethyl N-acetylphosphoramidothioate obtained above was added 100 g of toluene and the mixture was heated to 50° C. while stirring. Then the resulting was subjected to the same treatment as in Example 1 to give a crystal of O,S-dimethyl N-acetylphosphoramidothioate(purity: 89%, recovery rate of the crystal: 86%).

COMPARATIVE EXAMPLE 3

To 50 g of crude crystal O,S-dimethyl N-acetylphosphoramidothioate obtained in Preparation Example 1 above was added 100 g of methylene chloride and the mixture was heated to 40° C. while stirring to dissolve the crude product. Then the resulting was gradually cooled to 5° C. No crystal was obtained.

COMPARATIVE EXAMPLE 4

To 50 g of crude crystal O,S-dimethyl N-acetylphosphoramidothioate obtained above were added 15 g of methylene chloride, and the resultant solution was heated to dissolve the crystal under stirring. Then the solution was cooled gradually to 5° C. to crystallize, and the resultant crystal was filtered at the same temperature. The collected crystal was dried under reduced pressure to yield 28.8 g of O,S-dimethyl N-acetylphosphoramidothioate (purity 97.0%, purification yield 65%, Slurry concentration of the crystallization mass: 43%). The slurry was too viscous to transport.

PREPARATION EXAMPLE OF CRUDE O,S-DIMETHYL N-ACETYLPHOSPHORAMIDOTHIOATE 2

1292 Grams of 29% by weight of aqueous ammonia were added to a 2100 g of toluene solution containing 1608.6 g of O,O-dimethyl thiophosphoryl chloride at 50° C. over 40 min. The reaction solution was further kept at the same temperature for an hour and 359 g of water were added thereto and separated as a toluene layer and a water layer. The obtained water layer was extracted with 600 g of toluene at 50° C. The combined toluene solution was evaporated under reduced pressure to give 1506 g of O,O-dimethylphosphoramidothioate(purity: 86.3%).

19.1 Grams of dimethyl sulfate were gradually added to 296 g(purity 86.3%) of O,O-dimethylphosphoramidothioate at 40° C. in 30 min and to the resultant were further added 1180 g of O,O-dimethyl phosphoramidothioate and 76.1 g of dimethyl sulfate at the same temperature over 2 hours separately. The resultant reaction mixture was further maintained at the temperature for 8 hours to obtain 1562 g of O,S-dimethyl phosphoramidothioate(purity: 79.1%). To 1562 g of obtained O,S-dimethyl phosphoramidothioate was added 1218 g of acetic anhydride and 41 g of dimethyl sulfate at 40° C. over an hour. The resultant was maintained at the temperature for an hour to complete the reaction to give 2799 g of crude O,S-dimethyl N-acetylphosphoramidothioate(purity: 49.13%).

EXAMPLE 6

Purification solvent: Ethyl acetate (solubility of water: 3.6%)

556 Grams of water and then 741 g of 29% by weight of aqueous ammonia were added to 2000 g of crude O,S-dimethyl N-acetylphosphoramidothioate obtained above (purity: 49.13%) at 30° C. to adjust the pH of the solution to 7. The aqueous solution was extracted with 8992 g of ethyl acetate by continuous counter-current method to give 10272 g of ethyl acetate layer. The ethyl acetate layer was evaporated under reduced pressure to remove a part of the ethyl acetate, and 4504 g of a concentrate containing 20.5% by weight of O,S-dimethyl N-acetylphosphoramidothioate was obtained.

The concentrate was cooled under stirring from 40° to 10° C. in 3 hours and maintained at 10° C. for an hour. The crystallized product was filtered (slurry concentration: 14.3%) and dried under reduced pressure to give 646 g of 99.6% pure O,S-dimethyl N-acetylphosphoramidothioate as a white crystal. The crystallization yield was 69.6%. There was no difficulty to transport the slurry obtained after crystallization.

EXAMPLES 7–11

300 Grams of the crude O,S-dimethyl N-acetylphosphoramidothioate obtained in the "Preparation Example were treated according to the same procedure of Example 6 using the solvents listed in Table 2 to obtain a concentrated solution, of which concentration is listed in Table 2. There was no difficulty to transport the slurry obtained by crystallization. The results are summarized in Table 2 below.

TABLE 2

| Exp. No. | Solvent (Solubility of water) | Concentration before crystallization/Slurry | | Crystallization Yield/Purity | |
| --- | --- | --- | --- | --- | --- |
| 7 | Ethyl acetate (3.6%) | 30.8% | 24.9% | 80.5% | 99.2% |
| 8 | Methyl ethyl ketone (10%) | 43% | 18.6% | 43.3% | 97.8% |
| 9 | Methyl isobutyl ketone (1.9%) | 12.5% | 6.1% | 48.6% | 98.8% |
| 10 | Dimethyl carbonate (2.7%) | 33% | 22.3% | 67.6% | 98.8% |
| 11 | i-Butyl alcohol (18%) | 35% | 16.5% | 46.8% | 98.1% |

Extraction Using Dichloromethane 1

53.6 Grams of water and 70.8 g of 24% by weight of aqueous ammonia were added at 30° C. to 200 g of the crude O,S-dimethyl N-acetylphosphoramidothioate obtained in the Preparation Example 2 (purity: 49.13%) to give an aqueous solution of crude O,S-dimethyl N-acetylphosphoramidothioate, and the pH of the solution was adjusted to 7. Methylene chloride (330 g) was added to the aqueous solution and the resultant mixture was subjected to extraction to give 462 g of methylene chloride extract solution of which O,S-dimethyl N-acetylphosphoramidothioate content was 20.2% by weight. A part of the methylene chloride was distilled off under reduced pressure to give 180.6 g of a concentrated methylene chloride solution of which O,S-dimethyl N-acetylphosphoramidothioate content was 51.7% by weight. The methylene chloride solution was cooled in 3 hours from 30° to 18° C. at which temperature the slurry was transportable and then maintained at 18° C. for an hour. The crystallized product was collected by filtration (slurry concentration: 18.6%) and the crystal was dried under reduced pressure to give 33.6 g of 98.6% pure O,S-dimethyl N-acetylphosphoramidothioate as a white crystal. The crystallization yield was 35.6%.

Extraction Using Dichloromethane 2

90.3 Grams (content: 51.7%) of the concentrated methylene chloride solution obtained by the same method described above were cooled from 30° to 10° C. over 3 hours and then maintained at 10° C. for an hour. The crystallized product was collected by filtration (slurry concentration: 29.6%) and the crystal was dried under reduced pressure to give 26.6 g of 98.6% pure O,S-dimethyl N-acetylphosphoramidothioate of 98.6% purity as a white crystal. The crystallization yield was 56.2%. The slurry was extremely viscous and transport of it was difficult.

What is claimed is:

1. A method for purifying O,S-dimethyl N-acetylphosphoramidothioate, which comprises subjecting a crude crystal of O,S-dimethyl N-acetylphosphoramidothioate to recrystallization by using a two-phase solvent system comprising water and an organic solvent which is an aromatic hydrocarbon, an aliphatic carboxylic acid ester or an aliphatic ketone, wherein the amount of water is 0.1 to 2 parts by weight and the amount of organic solvent is 1 to 20 parts by weight to 1 part by weight of crude O,S-dimethyl N-acetylphosphoramidothioate.

2. A method according to claim 1, wherein the crude crystal of O,S-dimethyl N-acetylphosphoramidothioate is a crystallized product obtained by acetylating O,S-dimethylphosphoramidothioate with acetic anhydride in the presence of an acid catalyst and in the absence of a solvent, and then cooling the resulting reaction mixture.

3. A method according to claim 1, wherein the crude crystal of O,S-dimethyl N-acetylphosphoramidothioate is a crystallized product obtained by acetylating O,S-dimethylphosphoramidothioate with acetic anhydride in the presence of a solvent and an acid catalyst, and then cooling the resultant reaction mixture.

4. A method according to claim 1, wherein the crude crystal of O,S-dimethyl N-acetylphosphoramidothioate is a solid residue obtained by acetylating O,S-dimethylphosphoramidothioate with acetic anhydride in the presence of an acid catalyst and in the presence or absence of a solvent, and then concentrating the resulting reaction mixture.

5. A method according to claims 1, 3 or 4, wherein the aromatic hydrocarbon is benzene which is unsubstituted or substituted with one or more $C_1$–$C_4$ alkyl groups.

6. A method according to claim 5, wherein the organic solvent is benzene, toluene, xylene, ethylbenzene or cumene.

7. A method according to claims 1, 3 or 4 wherein the organic solvent is a $C_1$–$C_4$, alkyl ester of $C_1$–$C_4$ aliphatic carboxylic acid.

8. A method according to claims 1, 3 or 4 wherein the organic solvent is a $C_4$–$C_8$ aliphatic ketone.

* * * * *

UNITED STATES PATENT AND TRADEMARK OFFICE
Certificate

Patent No. 5,616,769                                                                                          Patented: April 1, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of the patent is: Yoji Sakito and Atukazu Iwata.

Signed and Sealed this Thirteenth Day of March, 2001.

THURMAN PAGE
*SPE*, Art Unit 1615
TC, 1600